US011457887B2

(12) United States Patent
Kakigi et al.

(10) Patent No.: US 11,457,887 B2
(45) Date of Patent: Oct. 4, 2022

(54) RADIOGRAPHIC IMAGING APPARATUS, RADIOGRAPHIC IMAGING SYSTEM, AND RECORDING MEDIUM

(71) Applicant: Konica Minolta, Inc., Tokyo (JP)

(72) Inventors: Takanori Kakigi, Kodaira (JP); Masahiro Kuwata, Machida (JP); Kentaro Hara, Hino (JP); Takeshi Saito, Hachioji (JP)

(73) Assignee: KONICA MINOLTA, INC., Tokyo (JP)

( * ) Notice: Subject to any disclaimer, the term of this patent is extended or adjusted under 35 U.S.C. 154(b) by 0 days.

(21) Appl. No.: 16/911,012

(22) Filed: Jun. 24, 2020

(65) Prior Publication Data

US 2021/0000441 A1 Jan. 7, 2021

(30) Foreign Application Priority Data

Jul. 3, 2019 (JP) .............................. JP2019-124167

(51) Int. Cl.
*A61B 6/00* (2006.01)
*H04N 5/32* (2006.01)

(52) U.S. Cl.
CPC ............ *A61B 6/563* (2013.01); *A61B 6/5258* (2013.01); *H04N 5/32* (2013.01)

(58) Field of Classification Search
None
See application file for complete search history.

(56) References Cited

U.S. PATENT DOCUMENTS

| 2006/0010498 A1* | 1/2006 | Oh ...................... G06F 16/9577 |
| | | 726/26 |
| 2008/0086757 A1* | 4/2008 | Pestoni ............ H04N 21/83555 |
| | | 726/2 |
| 2013/0263229 A1* | 10/2013 | Sugahara ............... A61B 6/548 |
| | | 726/4 |
| 2016/0232336 A1 | 8/2016 | Pitschel et al. |
| 2017/0242985 A1* | 8/2017 | Asahara .................. G06F 21/10 |

FOREIGN PATENT DOCUMENTS

| CN | 105306781 A | 2/2016 |
| JP | 2012-103645 A | 5/2012 |

OTHER PUBLICATIONS

IP India, Office Action/Search Report for the related Indian Application No. 202034026418, dated Jul. 13, 2021.

(Continued)

*Primary Examiner* — Edwin C Gunberg
(74) *Attorney, Agent, or Firm* — Lucas & Mercanti, LLP (57) ABSTRACT

A radiographic imaging apparatus includes a hardware processor. The hardware processor performs: image generation of generating a radiograph according to received radiation; a determination of whether a use permission condition for permitting use of the apparatus is satisfied; and when determining that the use permission condition is not satisfied, at least any one of specific operations of a first restriction operation of restricting operation of the apparatus, a second restriction operation of subjecting the generated radiograph to processing for restricting use of the radiograph, and a notification operation of providing a notification regarding the use permission condition.

20 Claims, 2 Drawing Sheets

(56) References Cited

OTHER PUBLICATIONS

CNIPA, Office Action for the related Chinese Application No. 202010625714.7, dated Sep. 1, 2021, with English translation.
CNIPA, Office Action for the related Chinese Application No. 202010625714.7, dated Feb. 28, 2022, with English translation.
CNIPA, Office Action for the related Chinese Application No. 202010625714.7, dated Jul. 13, 2022, with English translation.

* cited by examiner

FIG.1

RADIOGRAPHIC IMAGING APPARATUS, RADIOGRAPHIC IMAGING SYSTEM, AND RECORDING MEDIUM

CROSS-REFERENCE TO RELATED APPLICATIONS

The entire disclosure of Japanese Patent Application No. 2019-124167 filed on Jul. 3, 2019 is incorporated herein by reference in its entirety.

BACKGROUND

Technological Field

The present invention relates to a radiographic imaging apparatus, a radiographic imaging system, and a recording medium.

Description of the Related Art

A radiographic imaging system is expensive and therefore, some users of the radiographic imaging system pay for the system in installments while using it.

In the case of the installment payment, a user's delay in payment will disadvantage a seller of the system. In order to deal with such a nonpayment risk, sellers of the system conventionally have been managing licenses of the system. Specifically, in a common management method, a console centrally manages licenses including those of a plurality of radiographic imaging apparatuses in such a manner that the console makes an inquiry to a license management server via the Internet and only when their licenses are valid, permits the use of the console and the radiographic imaging apparatuses.

In addition, in recent years, some of radiographic imaging apparatuses included in a radiographic imaging system have been generalized (such as being compliant with a communication protocol of a console of each of various manufacturers) and others have been made communicable with a different manufacturer's product by using Software Development Kit (SDK). This has been leading to an increase of facilities that use radiographic imaging apparatus and a console of different manufactures in combination.

However, such a radiographic imaging apparatus allows a combination of different manufacturer's products and therefore, an illegal act may be able to be carried out such that a third party steals the radiographic imaging apparatus without permission and uses it by connecting it to another console.

A technique for dealing with stealing of the apparatus while dealing with nonpayment has been conventionally proposed.

For example, JP 2012-103645A discloses a radiographic imaging system which determines, while being able to receive a connection confirmation signal from a management server via an in-hospital LAN, that apparatuses (radiographic imaging apparatus and console) are connected to the in-house LAN and normally operate and; determines, when not being able to receive the connection confirmation signal, that the apparatuses are not connected to the in-house LAN, and restricts radiograph contents to be output (permits only display of a positioning confirmation image).

However, the radiographic imaging system described in JP 2012-103645A requires that the management server operates normally all the time. That is, when the management server fails or when communication between the radiographic imaging apparatus or console and the management server fails, confirmation of a license becomes impossible and therefore, even an authorized user who makes payment without delay will be restricted in the use thereof.

In addition, not only in the radiographic imaging system described in JP 2012-103645A, but also when a radiographic imaging apparatus is used in combination with a console of a different manufacturer, central license management of the radiographic imaging apparatus by the console, itself, becomes difficult.

SUMMARY

The present invention has been made in view of the above problems and it is an object of the present invention to establish, without using a management server, a mechanism that enables an authorized user to take and use a radiograph without limitation and that imposes restrictions on an unauthorized user in taking and using it To achieve at least one of the abovementioned objects, according to an aspect of the present invention, a radiographic imaging apparatus reflecting one aspect of the present invention comprises a hardware processor. The hardware processor performs: image generation of generating a radiograph according to received radiation; a determination of whether a use permission condition for permitting the use of the apparatus is satisfied; and when determining that the use permission condition is not satisfied, at least any one of specific operations of a first restriction operation of restricting operation of the apparatus, a second restriction operation of subjecting the generated radiograph to processing for restricting use of the radiograph, and a notification operation of providing a notification regarding the use permission condition.

To achieve at least one of the abovementioned objects, according to an aspect of the present invention, a radiographic imaging system reflecting one aspect of the present invention comprises: a radiographic imaging apparatus that includes a hardware processor capable of generating a radiograph according to received radiation, determining whether a use permission condition for permitting use of the apparatus is satisfied, and transmitting the generated radiograph to another apparatus; and a display apparatus that can display the radiograph received from the radiographic imaging apparatus. The hardware processor performs, when determining that the use permission condition is not satisfied, a restriction operation of restricting the use of the generated radiograph or a notification operation of providing a notification regarding the use permission condition.

BRIEF DESCRIPTION OF THE DRAWINGS

The advantages and features provided by one or more embodiments of the invention will become more fully understood from the detailed description given hereinbelow and the appended drawings which are given by way of illustration only, and thus are not intended as a definition of the limits of the present invention, wherein.

DETAILED DESCRIPTION OF THE EMBODIMENTS

Hereinafter, one or more embodiments of the present invention will be described with reference to the drawings. However, the scope of the invention is not limited to the disclosed embodiments.

1. First Embodiment

First, a first embodiment of the present invention will be described.

[1-1. Radiographic Imaging System]

First, a schematic configuration of a radiographic imaging system (hereinafter, system 100) according to an embodiment of the present invention will be described.

Figure 1:
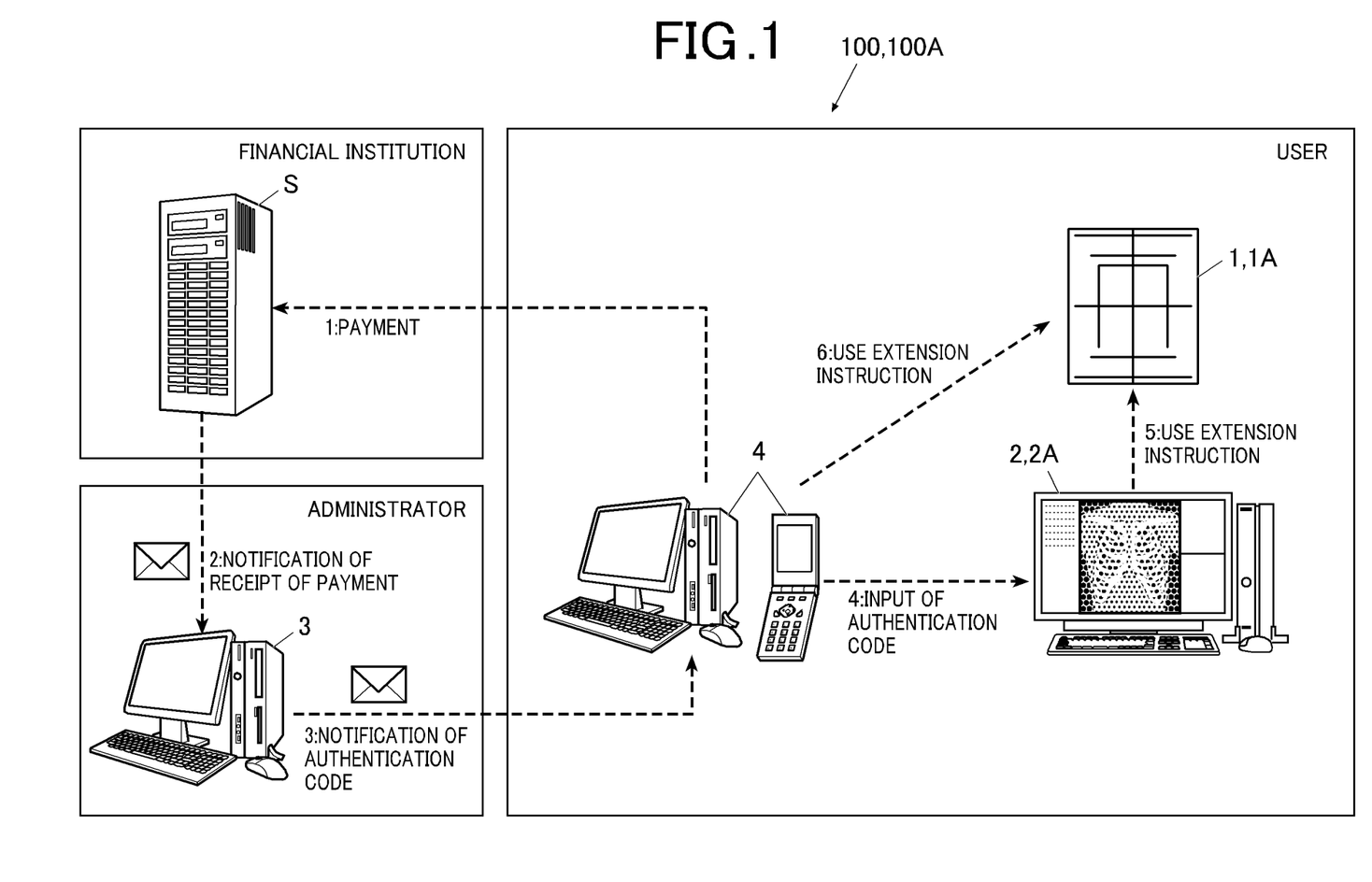
FIG. 1 shows a network diagram illustrating a radiographic imaging system according to a first embodiment (second embodiment) of the present invention.

FIG. 1 shows a network diagram illustrating the system 100.

It should be noted that reference signs in parentheses in FIG. 1 are those for a second embodiment described later.

The system 100 periodically receives a use permission (license), thereby allowing continuation of taking or using radiographs.

The system 100 includes one or a plurality of radiographic imaging apparatuses (hereinafter, radiographing apparatus 1), a console 2, a communication apparatus 4, and an authentication code issuing apparatus (hereinafter, issuing apparatus 3).

The radiographing apparatus 1 is irradiated with radiation from a radiation generator not illustrated and thereby can generate a radiograph of a subject (person, object) which is arranged between the radiographing apparatus 1 and the radiation generator.

Details of this radiographing apparatus 1 will be described later.

The console 2, which forms a display apparatus, can display the radiograph received from the radiographing apparatus 1.

In addition, the console 2 can receive an input of an authentication code.

Furthermore, the console 2 transmits, when receiving an input of the authentication code, a use extension instruction to the radiographing apparatus 1.

It should be noted that the system 100 may include a display apparatus for displaying a radiograph separately from the console 2.

Details of this console 2 will be described later.

The issuing apparatus 3 can issue an authentication code based on an operation by an administrator (a manufacturer, seller, owner, or the like of the system 100).

The issuing apparatus 3 according to the present embodiment transmits the issued authentication code to the communication apparatus 4.

The communication apparatus 4 is constituted of, for example, a PC, a portable terminal, or the like.

The communication apparatus 4 can receive the authentication code from the issuing apparatus 3.

The communication apparatus 4 according to the present embodiment can display the received authentication code on a display.

It should be noted that the system 100 may be configured such that the communication apparatus 4 is integrated with the console 2 or conversely, the communication apparatus 4 also serves the function of the console 2.

In addition, the system 100 may be configured such that the communication apparatus 4 forms a display apparatus.

Furthermore, the system 100 may be configured such that when the communication apparatus 4 receives the authentication code, the communication apparatus 4 transmits a use extension instruction to the radiographing apparatus 1.

The system 100 according to the present embodiment can connect with the server S of a financial institution via the Internet.

Therefore, a user can make a payment online by using the communication apparatus 4.

Furthermore, the system 100 can receive, in real time, a notification of receipt of payment from the financial institution for every payment and therefore an administrator who operates the issuing apparatus 3 does not need to contact the financial institution in order to confirm the payment.

It should be noted that payment and the reception of a notification of receipt of the payment may be performed via an actual store (person) of the financial institution.

[1-2. Radiographic Imaging Apparatus]

Figure 2:
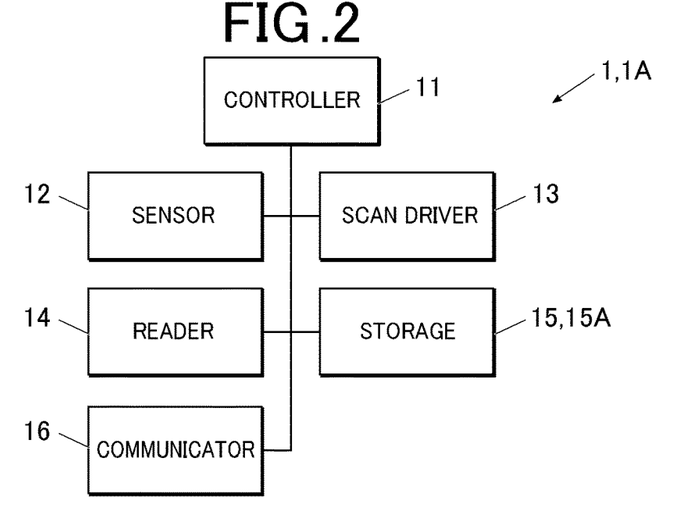
FIG. 2 shows a block diagram illustrating a radiographic imaging apparatus included in the radiographic imaging system in FIG. 1.

Next, details of the radiographing apparatus 1 included in the above described system 100 will be described. FIG. 2 shows a block diagram illustrating the radiographing apparatus 1.

It should be noted that reference signs in parentheses in FIG. 2 are those for the second embodiment described later.

(1-2-1. Configuration)

The radiographing apparatus 1 includes a controller 11, a sensor 12, a scan driver 13, a reader 14, a storage 15, and a communicator 16.

The components 11 to 16 are electrically connected by a bus or the like.

The controller 11 includes a central processing unit (CPU) and a random access memory (RAM) which are not illustrated.

The CPU reads various processing programs which are stored in the storage 15, develops them to the RAM, and executes various processes according to the processing programs, thereby centrally controlling the operations of the components of the radiographing apparatus 1.

The sensor 12 includes a scintillator and a photoelectric conversion panel which are not illustrated.

The scintillator is formed of, for example, columnar crystals of CsI or the like in a flat plate shape.

In addition, the scintillator emits, by receiving radiation, an electromagnetic wave (for example a visible light, or the like) having a wavelength longer than the radiation at an intensity according to a dose of the received radiation.

Furthermore, the scintillator is arranged so as to extend in parallel to a radiation incident surface of a housing which is not illustrated.

The photoelectric conversion panel includes a substrate and a plurality of pixels arranged in a two-dimensional form (for example, in a matrix form) on a surface of a substrate.

Each of the pixels includes: a semiconductor element that generates electric charges of an amount according to the intensity of the electromagnetic wave generated by the scintillator; and a switch element that is provided between the semiconductor element and wiring which is connected to the reader 14.

Furthermore, the photoelectric conversion panel is arranged so as to extend in parallel to the radiation incident surface and scintillator on a side opposite to a side where the radiation incident surface of the scintillator exists.

The scan driver 13 can switch on/off each of the switch elements.

The reader 14 can read the amount of electric charges emitted from each of the pixels, as a signal value and generate image data of a radiograph based on a plurality of read signal values.

The storage 15, which is constituted of a hard disk drive (HDD), a semiconductor memory, or the like, stores processing programs for executing various processes, parameters required for executing the processing programs, files, and the like.

In addition, the storage 15 can store the image data of the radiograph.

The communicator 16 can transmit and receive various signals and various data items to and from another apparatus (for example, the console 2) that is connected via a communication network N (such as a local area network (LAN), wide area network (WAN), the Internet, or the like).

(1-2-2. Operation)

The controller 11 of the radiographing apparatus 1 thus configured controls the scan driver 13 and the reader 14 so as to generate a radiograph according to received radiation That is, the controller 11 forms an image generator.

In addition, the controller 11 causes the storage 15 to store the image data of the radiograph.

In addition, the controller 11 can execute output processing after generating the radiograph.

The controller 11 according to the present embodiment transmits, in this output processing, the radiograph to another apparatus (for example, the console 2) via the communicator 16

It should be noted that the radiographing apparatus 1 itself may include a display which is not illustrated and in this output processing, the controller 11 may cause the display to display the radiograph.

The controller 11 executes this output processing, thus forming an outputter.

In addition, the controller 11 according to the present embodiment executes conditional update processing when a predetermined condition is satisfied.

In this conditional update processing, the controller 11 updates a use permission condition.

The "use permission condition" according to the present embodiment is, for example, the permitted number of days of use or the permitted number of pieces generated.

The "permitted number of days of use" is the remaining number of days for which the radiographing apparatus 1 can be normally used.

In addition, the "permitted number of pieces generated" is the remaining number of radiographs which the radiographing apparatus 1 can generate.

When the use permission condition is the "permitted number of days of use," each time, for example, when a power is turned on for the first time of a day or a date of a timer is updated, the permitted number of days of use is decremented or the number of days of use is incremented. It should be noted that the number of days may be a period for which the power is on or may be a period simply according to the number of days that have elapsed from an installation date in consideration of a deterioration over time.

On the other hand, when the use permission condition is the "permitted number of pieces generated," each time a radiograph is generated, the permitted number of pieces generated is decremented or the number of generated radiographs is incremented. It should be noted that instead of the number of times a radiograph is generated, the number of times radiation irradiation is detected may be used for determination.

In addition, whether connection with the communication apparatus 4 is established may be used as a use permission condition. In this case, connection with the issuing apparatus 3 and a financial institution is not necessary.

In addition, the controller 11 also executes condition update processing when receiving a use extension instruction from the console 2 or the communication apparatus 4.

In this case, the controller 11 increases the permitted number of days of use or the permitted number of pieces generated according to a content of the received use extension instruction; or decreases the number of days of use or the number of generated radiographs according to the content of the received use extension instruction.

Figure 3:
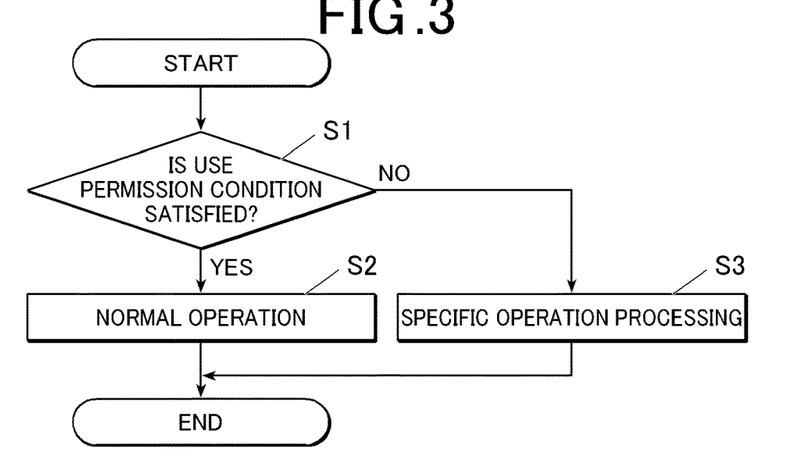
FIG. 3 shows a flowchart illustrating a flow of processing executed by the radiographic imaging apparatus in FIG. 2.

When a predetermined condition is satisfied (for example, when the power is turned on, connection with the console 2 is established, a predetermined control signal is received from the console 2, a radiograph is generated, or the like), the controller 11 executes determination processing shown in FIG. 3 (step S1).

In this determination processing, the controller 11 determines whether a use permission condition for permitting the use of the apparatus is satisfied.

In the present embodiment, "the use permission condition is satisfied" indicates, for example, that the number of days for which the radiographing apparatus 1 itself has been used so far is equal to or less than a predetermined permitted number of days of use or that the number of radiographs which have been generated so far is equal to or less than a predetermined permitted number of pieces generated.

In addition, when the use permission condition is whether connection with the communication apparatus 4 is established, "the use permission condition is satisfied" indicates that the communication apparatus 4 has been connected.

The controller 11 executes this determination processing, thus forming a determiner.

Furthermore, when determining that the use permission condition is satisfied (when determining that the number of days of use is equal to or less than the permitted number of days of use or when determining that the number of generated radiographs is equal to or less than the permitted number of pieces generated, step S1: Yes), the controller 11 performs a normal operation (step S2).

On the other hand, when determining that the use permission condition is not satisfied (when determining that the number of days of use is not equal to or less than the permitted number of days of use or when determining that the number of generated radiographs is not equal to or less than the permitted number of pieces generated, step S1: No), the controller 11 performs specific operation processing (step S3).

In this specific operation processing, the controller 11 according to the present embodiment performs at least either one of a first restriction operation and a notification operation.

In the "first restriction operation," the operation of the radiographing apparatus 1 itself is restricted. Restrictions on this "operation of the radiographing apparatus 1 itself" include, for example, an output restriction, a generation restriction, a storage restriction, and the like.

The "output restriction" refers to restricting the output of a radiograph (transmission of image data, display on the display, and the like).

The "generation restriction" refers to restricting the generation of a radiograph (accumulation of electric charges, reading by the reader, and the like).

The "storage restriction" refers to restricting the storage of image data of a radiograph to the storage 15.

In restricting the output of a radiograph, preferably, a generated radiograph is stored in the storage 15 and when a use extension instruction is received from the console 2, the image data of the stored radiograph is output.

By doing so, even if a user erroneously takes a radiograph in a state where a use permission condition is not satisfied (especially when an Auto Exposure Detect (AED) function is installed in the radiographing apparatus 1, the radiographing apparatus 1 can generate a radiograph by itself without communicating with the console 2 and therefore, such radiographing is more likely to be performed), the radiograph can be output when the use permission condition is satisfied thereafter, which can prevent a subject from being irradiated in vain.

In addition, in restricting the output of a radiograph, preferably, another image instead of a radiograph (for example, a dummy image that imitates a radiograph or a white image in which signal values of all pixels thereof are zero) is output.

This allows the user to verify, by viewing the other image, that the radiographing apparatus 1 or the console 2 is running, which can prevent the user from misrecognizing that the radiographing apparatus 1 or the console 2 fails.

Furthermore, as the other image, an image on which a message asking for payment is written may be output. This allows the user to recognize that the use permission condition is not satisfied.

In addition, in storing image data of another image in the storage 15 or transmitting it to the console 2, an image management number (for example, 005 or the like) of a corresponding normal radiograph may be given to the other image so as to allow replacement with the radiograph after the use permission condition is satisfied again. This allows consistent image management to be performed on the radiographing apparatus 1 or the console 2.

The controller 11 executes this specific operation processing, thus forming a specific operator.

In addition, when the use permission condition is whether connection with the communication apparatus 4 is established, a restriction content may be varied according to an apparatus being connected.

Figure 4:
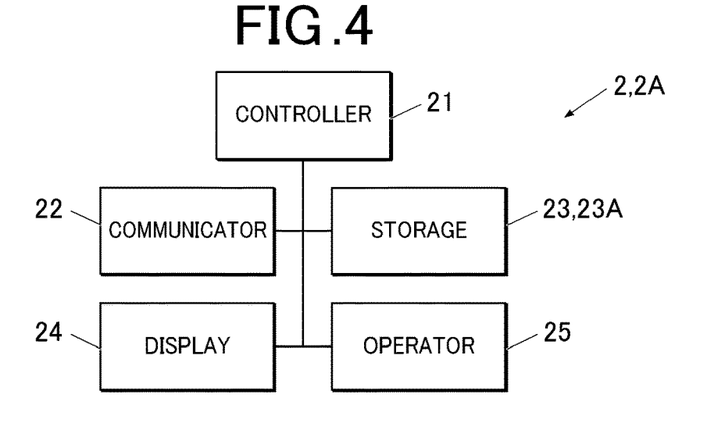
FIG. 4 shows a block diagram illustrating a display apparatus included in the radiographic imaging system in FIG. 1.

By execution of such specific operation processing by the controller 11, a radiograph is not displayed on the unillustrated display which is included in the radiographing apparatus 1 itself, or a display 24 of the console 2, unless the use permission condition is satisfied.

In the "notification operation," a notification regarding the use permission condition is provided.

Specifically, it is notified: whether the use permission condition is satisfied; that an action to satisfy the use permission condition (for example, payment) is encouraged; or that the operation of the radiographing apparatus 1 itself or the system 100 is restricted.

The notification is performed by, for example, displaying on the unillustrated display that is included in the radiographing apparatus 1, a voice output from an unillustrated speaker that is included in the radiographing apparatus 1, illumination of an unillustrated lamp that is included in the radiographing apparatus 1, or the like.

When the use permission condition is whether connection with the communication apparatus 4 is established, it is notified: that connection with the communication apparatus 4 is not established or that connection with an apparatus different from the communication apparatus 4 is established.

When the unillustrated display, lamp, or the like which is included in the radiographing apparatus 1 is set to always provide some kind of notification (even when the use permission condition is satisfied), the controller 11 may change, for the notification operation, an aspect of the notification (a display content on the display, flashing or color of the lamp) to be different from the one in a case where the use permission condition is satisfied.

In addition, in notifying that the use permission condition is satisfied, the controller 11 may notify it together with the remaining permitted number of days of use or the remaining permitted number of pieces generated.

Furthermore, the controller 11 may perform the notification operation in parallel with the first restriction operation.

Yet furthermore, the controller 11 may transmit information required for the notification operation to the console 2 or the communication apparatus 4 so as to make the console 2 or the communication apparatus 4 perform the abovementioned notification operation. In this case, a function of the radiographing apparatus 1 performing the notification operation becomes unnecessary.

Alternatively, both the radiographing apparatus 1 and the console 2 may perform the notification operation.

[1-3. Console]

Next, details of the console 2 included in the above system 100 will be described.

FIG. 4 shows a block diagram illustrating the console 2.

It should be noted that reference signs in parentheses in FIG. 4 are those for the second embodiment described later.

(1-3-1. Configuration)

The console 2 according to the present embodiment includes, as shown in FIG. 4, a controller 21, a communicator 22, a storage 23, a display 24, and an operator 25.

The components 21 to 25 are electrically connected by a bus or the like.

The controller 21 is constituted of a CPU, a RAM, and the like.

The CPU of the controller 21 reads various processing programs stored in the storage 23, develops them into the RAM, and executes the various processes according to the developed programs, thereby centrally controlling the operations of the components of the console 2.

The communicator 22 can transmit and receive various signals and various data items to and from another apparatus (for example, the radiographing apparatus 1) that is connected via the communication network N (such as LAN, WAN, the Internet, or the like).

The storage 23 is constituted of a nonvolatile semiconductor memory, a hard disk, or the like.

In addition, the storage 23 stores various programs executed by the controller 21 and parameters required for executing the programs, and the like.

In addition, the storage 23 may be able to store a radiograph.

The display 24 is constituted of a monitor that displays an image, such as a liquid crystal display (LCD) or a cathode ray tube (CRT).

In addition, the display 24 displays various images and the like, based on a control signal which is input from the controller 21.

The operator 25 according to the present embodiment is constituted of: a keyboard including cursor keys, a numerical keypad, and various function keys, and the like; a pointing device such as a mouse; a touch panel laminated on a surface of the display 24; and the like.

In addition, the operator 25 outputs a control signal according to an operation performed by a user, to the controller 21.

(1-3-2. Operation)

The controller 21 of the console 2 thus configured causes, when receiving image data from the radiographing apparatus 1, the display 24 to display various images based on the image data.

When the radiographing apparatus 1 transmits image data of a normal radiograph without performing a specific operation, the radiograph is displayed.

On the other hand, when the radiographing apparatus 1 performs a specific operation and transmits image data of another image (dummy image or write image), the other image is displayed.

In addition, the controller 21 according to the present embodiment stores the received image data in the storage 23 in an order of image management numbers given to the image data.

When the controller 21 receives, while image data of a white image is stored in the storage 23, image data of a radiograph to which a number identical to an image management number of the white image is given, it may replace the image data of the white image with the image data of the radiograph.

In addition, the controller 21 manages a use permission condition.

When the use permission condition is the "permitted number of days of use," the permitted number of days of use is decremented or the number of days of use is incremented each time a date of the timer is updated.

On the other hand, when the use permission condition is the "permitted number of pieces generated," the permitted number of pieces generated is decremented or the number of generated radiographs is incremented each time a radiograph is generated.

In addition, when the use permission condition is getting close to being unsatisfied, (for example, when the permitted number of days of use or the permitted number of pieces generated becomes a predetermined value or less), the controller 21 provides a notification thereof.

The notification is provided by, for example, displaying on the display 24, a voice output from an unillustrated speaker that is included in the console 2, illumination of an unillustrated lamp that is included in the console 2, or the like.

In addition, the controller 21 receives an input of an authentication code, based on an operation performed for the operator 25.

Furthermore, the controller 21 executes, when receiving an input of a correct authentication code, condition update processing.

In this condition update processing, the controller 21 increases the permitted number of days of use or the permitted number of pieces generated according to the input authentication code; or decreases the number of days of use or the number of generated radiographs according to the input authentication code.

Moreover, the controller 21 transmits, in the condition update processing, a use extension instruction to the radiographing apparatus 1.

In addition, the controller 21 may restrict, when determining that the use permission condition is not satisfied, the operation of the console 2.

Furthermore, the controller 21 may perform a notification operation by receiving information required for the notification operation from the radiographing apparatus 1.

Specifically, it notifies: whether the use permission condition is satisfied; that an action to satisfy the use permission condition is encouraged; or that the operation of the radiographing apparatus 1 or the system 100 itself is restricted.

The notification is performed by, for example, displaying on the display 24, a voice output from an unillustrated speaker that is included in the console 2, illumination of an unillustrated lamp that is included in the console 2, or the like.

[1-4. Effects]

The system 100 according to the present embodiment described above is configured such that the radiographing apparatus 1 itself determines whether the use permission condition is satisfied and a management server dedicated to managing the use permission condition is not required. This allows an authorized user to continue using the radiographing apparatus 1 even when a malfunction occurs in the communication network N.

In addition, when the use permission condition is no longer satisfied (the permitted number of days of use becomes 0 or the permitted number of pieces generated becomes 0), the radiographing apparatus 1 executes specific operation processing (performs at least either one of the first restriction operation and the notification operation). When performing the first restriction operation, it disables taking and using a radiograph and shortly thereafter, it disables itself. On the other hand, when performing the notification operation, it lets even other persons therearound know that the use permission condition is not satisfied. Therefore, providing the radiographing apparatus 1 with a function of executing the specific operation processing can deter those who try to steal it from stealing.

Therefore, using the radiographing apparatus 1 allows such a system 100 to be established without using a management server, that includes a mechanism for enabling an authorized user to take and use a radiograph without limitation and for imposing restrictions on an unauthorized user in taking and using it.

2. Second Embodiment

Next, the second embodiment of the present invention will be described.

Here, configurations similar to those in the above first embodiment are denoted by the same reference signs and descriptions thereof will be omitted.

In the system 100 according to the first embodiment described above, the radiographing apparatus 1 performs the first restriction operation so as to perform a restriction operation of restricting the use of a generated radiograph; however, in a radiographic imaging system according to the present embodiment (hereinafter, system 100A), a radiographic imaging apparatus (hereinafter, radiographing apparatus 1A) and a console 2 cooperatively perform the restriction operation.

[2-1. Radiographic Imaging Apparatus]

First, differences between the radiographing apparatus 1A included in the system 100A according to the present embodiment and the radiographing apparatus 1 according to the first embodiment described above will be described.

The radiographing apparatus 1A is different from the radiographing apparatus 1 according to the first embodiment described above in contents of specific operation processing which is executed when it is determined in the determination processing that the use permission condition is not satisfied (a program stored in a storage 15A (see FIG. 2) is different from one stored in the storage 15 according to the first embodiment described above).

In this specific operation processing, a controller 11 according to the present embodiment performs at least either one of a second restriction operation and a notification operation.

In the second restriction operation, the generated radiograph is subjected to processing for restricting the use thereof.

This "processing for restricting the use" includes, for example, lowering of an image quality, encryption, addition of information, and the like.

The "lowering of an image quality" refers to lowering a pixel density or resolution of the radiograph (generating a low quality image).

The "encryption" refers to encrypting image data of the radiograph.

The "addition of information" refers to adding, to the image data of the radiograph, display restriction information (for example, a flag) to instruct the console 2A (another apparatus) to restrict display of the radiograph.

In storing image data of the low quality image in the storage 15 or transmitting it to the console 2, an image management number (for example, 005 or the like) of a corresponding normal radiograph may be given to the low quality image so as to allow replacement with the radiograph after the use permission condition is satisfied again. This allows consistent image management to be performed on the radiographing apparatus 1 or the console 2.

The controller 11 executes output processing in such a manner, thus forming at least either one of an image quality adjuster, an encrypter, and an information adder.

The radiographing apparatus 1A according to the present embodiment also may perform the first restriction operation and the notification operation together which are executed by the radiographing apparatus 1 of the first embodiment.

In addition, the radiographing apparatus 1 according to the first embodiment may perform the second restriction operation according to the present embodiment, together.

[2-2. Console]

Next, differences between the console 2A included in the system 100A according to the present embodiment and the console 2 according to the first embodiment described above will be described.

The console 2A is different from the console 2 according to the first embodiment described above in an operation performed after receiving image data from the radiographing apparatus 1 (a program stored in a storage 23A (see FIG. 4) is different from one stored in the storage 23 according to the first embodiment described above).

A controller 21 of the console 2A executes, when receiving image data from the radiographing apparatus 1, processing according to a state of the image data.

When the radiographing apparatus 1 is set to encrypt image data and the received image data has been encrypted, the controller 21 does not cause the display 24 to display a radiograph.

In addition, when the radiographing apparatus 1 is set to add display restriction information to image data and the display restriction information has been added to the received image data, the controller 21 does not cause the display 24 to display a radiograph.

Furthermore, when the received image data is image data of a normal radiograph or image data of a low quality image, the controller 21 causes the display 24 to display the normal radiograph or the low quality image.

When received image data has been encrypted or display restriction information has been added to the received image data, the controller 21 causes, on receipt of an input of an authentication code, the display 24 to display a radiograph by encoding the image data or removing the display restriction information.

The controller 21 and the controller 11 of the above radiographing apparatus 1A form a specific operator in which the controller 11 of the radiographing apparatus 1A executes the above specific operation processing and the controller 21 executes processing according to a state of the image data.

When the radiographing apparatus 1A transmits image data of another image (dummy image or write image), a radiograph or the other image may be displayed on the display 24.

[2-3. Effects]

With the radiographing apparatus 1A and the console 2A according to the present embodiment described above, such a system 100 can be established without using a management server, that includes a mechanism for enabling an authorized user to take and use a radiograph without limitation and for imposing restrictions on an unauthorized user in taking and using a radiograph as with the above first embodiment.

3. Examples

The present invention has been described based on the embodiments so far; however, the present invention can be appropriately modified without departing from the gist thereof.

For example, techniques described below can be added to the systems 100 and 100A respectively according to the first and second embodiments.

(3-1. First Example)

Some users have difficulty in making one payment even when payment for the system 100, 100A is to be made by installments.

In view of such a problem, it also may be possible that in the system 100, 100A according to the first, second embodiment, whether the use permission condition is satisfied is determined for each of apparatuses that constitute the system 100, 100A (for example, the radiographing apparatus 1, 1A and the console 2, 2A) and when it is determined to be satisfied, the use of the corresponding apparatus is permitted.

In addition, it also may be possible that whether the use permission condition is satisfied is determined before each use of a function (for example, a function of executing specific image processing) and when it is determined to be satisfied, the use of the corresponding function is permitted.

This allows payment for the system 100, 100A to be made installments for each apparatus or each function; and therefore, a user thereof can minimize the payment by making payment for only a minimum required apparatus or function. Thus, the user can relatively easily continue the payment.

(3-2. Second Example)

In the system 100, the radiographing apparatus 1 and the console 2, 2A cooperatively operate and therefore, if each of them independently manages a use permission condition, their management contents may differ, for example; resulting in more time and effort spent on the management.

In view of such a problem, it also may be possible that in the system 100, 100A according to the first, second embodiment, when an authentication code is input to the console 2, 2A, a use permission condition managed by the console 2, 2A and a use permission condition managed by the radiographing apparatus 1 can be updated to an identical content at a time.

If a plurality of the radiographing apparatuses 1, 1A are included in the system 100, use permission conditions for all of the radiographing apparatuses 1, 1A are updated.

This facilitates management of use permission conditions.
(3-3. Third Example)

There may be a case, for example, where a user has taken a radiograph with a use permission condition unsatisfied since the user does not intend to immediately use a radiograph; however, a person who is its subject makes a request to view the radiograph and accordingly, the user is suddenly required to make payment but has difficulty in immediately preparing for the payment due to high cost.

In view of such a problem, it may be possible that in the system 100, 100A according to the first, second embodiment described above, the payment is divided for each radiograph and when payment has been made only for a specific radiograph; the use of only the specific radiograph is permitted.

Specifically, the issuing apparatus 3 may be configured to be able to receive an input of an image management number and also configured to be able to create a specific authentication code that allows the use of only a radiograph with an input image management number.

In addition, the radiographing apparatus 1, 1A may be configured to remove, when the specific authentication code is input to the console 2, 2A, a restriction on a corresponding radiograph.

This allows the user to use only a desired radiograph by notifying an administrator of the image management number of the radiograph which the user desires to use and making payment only for the use of the radiograph at a financial institution. Therefore, even in a case where a predetermined payment is impossible, necessary radiographs can be used.
(3-4. Fourth Example)

For a user of the system 100, 100A, regular payment processing is troublesome work.

In view of such a problem, it may be possible that in the system 100, 100A according to the first, second embodiment described above, the payment is made through the console 2, 2A or the communication apparatus 4.

Specifically, an application of a financial institution may be installed, for example, in the console 2, 2A or the communication apparatus 4 associated with the radiographing apparatus 1, 1A, thereby allowing payment processing via the Internet.

This allows a burden on the user in the payment processing to be significantly reduced.

In addition, the console 2, 2A may receive an authentication code from the issuing apparatus 3 and perform an automatic input.

Furthermore, the issuing apparatus 3 may be configured to automatically issue an authentication code when receiving the notification of receipt of the payment from the financial institution.

This allows a burden involved in procedures required for use extension, including the payment processing, to be significantly reduced.
(3-5. Fifth Example)

Restricting the operation of the radiographing apparatus 1 can be a deterrent to stealing. However, if the radiographing apparatus 1 is stolen, it will be very difficult to find it out.

In view of such a problem, it may be possible that in the system 100, 100A according to the first, second embodiment described above, the radiographing apparatus 1, 1A is provided with a location tracking function.

Specifically, a receiver for receiving a radio wave from a Global Positioning System (GPS) satellite may be incorporated into the radiographing apparatus 1.

This allows the radiographing apparatus 1, if stolen, to be easily found out.

In addition, it may be possible that the receiver is connected to a cloud server and the console 2 via the Internet to allow GPS data to be periodically transmitted from the receiver to the console 2; and when it is determined that the cloud server and the console 2 cannot receive the GPS data, cancellation of a use permission is notified to the radiographing apparatus 1, 1A and the radiographing apparatus 1, 1A performs a specific operation.

The transmission frequency of the GPS data is not necessary for each radiographing but it is only required to be once a day.

This disables taking and using a radiograph without waiting for the use permission condition to become unsatisfied; and therefore, can be a strong deterrent to stealing.

In addition, at least either GPS data or a serial number of the radiographing apparatus 1 may be added to the image data of a generated radiograph.

This allows an unauthorized use of the radiographing apparatus 1, 1A to be easily detected by checking the radiograph.

Furthermore, in the above description, an example of using a hard disk, a nonvolatile semiconductor memory, or the like as a computer-readable medium of the program according to the present invention has been disclosed; however, this example is not limited thereto. As an alternate computer readable medium, a portable recording medium such as a CD-ROM can be used. In addition, as a medium for providing program data according to the present invention via a communication line, a carrier wave can also be used.

Although embodiments of the present invention have been described and illustrated in detail, the disclosed embodiments are made for purposes of illustration and example only and not limitation. The scope of the present invention should be interpreted by terms of the appended claims.

What is claimed is:

1. A radiographic imaging apparatus comprising a hardware processor, wherein
the hardware processor performs:
image generation of generating a radiograph according to received radiation;
a determination of whether a use permission condition for permitting use of the radiographic imaging apparatus is satisfied, wherein the use permission condition is a permitted number of days of use or a permitted number of radiographs generated and the hardware processor updates the use permission condition;
an update of the use permission condition by:
decrementinq the permitted number of days of use or incrementing a number of days of use in response to power being turned on for a first time of a day or a date of a timer is updated during use; or
decrementinq the permitted number of radiographs generated or incrementing a number of generated radiographs in response to the image generation of a radiograph; and when determining that the use permission condition is not satisfied, at least any one of specific operations:
a first restriction operation of restricting operation of the radiographic imaging apparatus;
a second restriction operation of subjecting the generated radiograph to processing for restricting use of the radiograph; and
a notification operation of providing a notification regarding the use permission condition.

2. The radiographic imaging apparatus according to claim 1, wherein
the hardware processor determines whether a number of days for which the radiographic imaging apparatus has been used so far is equal to or less than a predetermined permitted number of days of use; and performs, when determining that the number is not equal to or less than the permitted number of days of use, at least any one of operations of the first restriction operation, the second restriction operation, and the notification operation.

3. The radiographic imaging apparatus according to claim 1, wherein
the hardware processor determines whether a number of radiographs which have been generated so far is equal to or less than a predetermined permitted number of pieces generated; and performs, when determining that the number is not equal to or less than the permitted number of pieces generated, at least any one of operations of the first restriction operation, the second restriction operation, and the notification operation.

4. The radiographic imaging apparatus according to claim 1, wherein
the hardware processor outputting the radiograph restricts output of the radiograph as the first restriction operation.

5. The radiographic imaging apparatus according to claim 4, wherein
the hardware processor outputs, when restricting the output of the radiograph, another image instead of the radiograph.

6. The radiographic imaging apparatus according to claim 4, wherein
the hardware processor adjusting a pixel density or resolution of the radiograph lowers the pixel density or resolution of the radiograph as the second restriction operation.

7. The radiographic imaging apparatus according to claim 4, wherein
the hardware processor encrypts image data of the radiograph as the second restriction operation.

8. The radiographic imaging apparatus according to claim 4, wherein
the hardware processor capable of transmitting the radiograph to another apparatus adds display restriction information to image data of the radiograph, the display restriction information instructing the other apparatus to restrict display of the radiograph, and adds a display restriction flag as the second restriction operation.

9. The radiographic imaging apparatus according to claim 1, wherein
the hardware processor restricts generation of the radiograph as the first restriction operation.

10. The radiographic imaging apparatus according to claim 1, wherein
the hardware processor capable of causing a storage to store image data of the radiograph restricts storage of the image data in the storage as the first restriction operation.

11. The radiographic imaging apparatus according to claim 1, wherein
the hardware processor notifies as the notification operation: whether the use permission condition is satisfied; that an action to satisfy the use permission condition is encouraged; or that the operation of the radiographic imaging apparatus is restricted.

12. The radiographic imaging apparatus according to claim 1, wherein
the use permission comprises a license allowing continuation of taking or using radiographs by the radiographic imaging apparatus.

13. The radiographic imaging apparatus according to claim 1, wherein
the hardware processor adjusting a pixel density or resolution of the radiograph lowers the pixel density or resolution of the radiograph as the second restriction operation.

14. The radiographic imaging apparatus according to claim 1, wherein
the use permission condition is the permitted number of days of use and the hardware processor updates the use permission condition by decrementing the permitted number of days of use or incrementing a number of days of use in response to power being turned on for a first time of a day or a date of a timer is updated.

15. The radiographic imaging apparatus according to claim 1, wherein
the use permission condition is the permitted number of radiographs generated and the hardware processor updates the use permission condition by decrementing the permitted number of radiographs generated or incrementing a number of generated radiographs in response to the image generation of a radiograph.

16. A radiographic imaging system comprising:
a radiographic imaging apparatus comprising a hardware processor capable of generating a radiograph according to received radiation, determining whether a use permission condition for permitting use of the radiographic imaging apparatus is satisfied, and transmitting the generated radiograph to another apparatus, wherein the use permission condition is a permitted number of days of use or a permitted number of radiographs generated and the hardware processor updates the use permission condition; and
a display apparatus capable of displaying the radiograph received from the radiographic imaging apparatus;
wherein the hardware processor updates the use permission condition by:
decrementinq the permitted number of days of use or incrementing a number of days of use in response to power being turned on for a first time of a day or a date of a timer is updated during use; or
decrementinq the permitted number of radiographs generated or incrementing a number of generated radiographs in response to the image generation of a radiograph; and
wherein the hardware processor performs, when determining that the use permission condition is not satisfied, a restriction operation of restricting use of the generated radiograph or a notification operation of providing a notification regarding the use permission condition.

17. The radiographic imaging system according to claim 16, wherein
the hardware processor restricts display of the radiograph on the display apparatus as the restriction operation.

18. The radiographic imaging system according to claim 16, wherein
the hardware processor causes, as the notification operation, the display apparatus to display: whether the use permission condition is satisfied; that an action to satisfy the use permission condition is encouraged; or that operation of the radiographic imaging system is restricted.

19. The radiographic imaging system according to claim 16, wherein
the display apparatus is part of at least one of a console or a communication apparatus that receives an authentication code from an issuing apparatus of an administrator of the system through a communication network and sends a use extension instruction to the radiographic imaging apparatus in response to receipt of the authentication code, and
the hardware processor of the radiographic imaging apparatus updates the user permission condition in response to receipt of the use extension instruction by incrementing the permitted number of days of use, decrementing a number of days of use, incrementing the permitted number of radiographs generated, or decrementing a number of generated radiographs.

20. A computer-readable recording medium storing a program, wherein
the program causes a radiographic imaging apparatus to execute processing, the radiographic imaging apparatus comprising a hardware processor that generates a radiograph according to received radiation,
the processing including
update processing of updating the use permission condition by:
decrementing the permitted number of days of use or incrementing a number of days of use in response to power being turned on for a first time of a day or a date of a timer is updated during use, or
decrementing the permitted number of radiographs generated or incrementing a number of generated radiographs in response to the image generation of a radiograph,
determination processing of determining whether a use permission condition for permitting use of the radiographic imaging apparatus is satisfied, wherein the use permission condition is a permitted number of days of use or a permitted number of radiographs generated and the hardware processor updates the use permission condition, and
specific operation processing that is performed when it is determined in the determination processing that the use permission condition is not satisfied, the specific operation processing causing at least any one of operations to be performed,
the operations including
a first restriction operation of restricting operation of the apparatus,
a second restriction operation of subjecting the radiograph generated by an image generator to processing for restricting use of the radiograph, and
a notification operation of providing a notification regarding the use permission condition.

* * * * *